(12) United States Patent
Videman

(10) Patent No.: US 11,272,856 B2
(45) Date of Patent: Mar. 15, 2022

(54) MEASURE OF DISC DEGENERATION AND PATHOLOGY

(71) Applicants: Keijo Tapio Videman, Chapel Hill, NC (US); Michele Crites Battie, Chapel Hill, NC (US)

(72) Inventor: Keijo Tapio Videman, Chapel Hill, NC (US)

( * ) Notice: Subject to any disclaimer, the term of this patent is extended or adjusted under 35 U.S.C. 154(b) by 1720 days.

(21) Appl. No.: 14/855,377

(22) Filed: Sep. 15, 2015

(65) Prior Publication Data

US 2016/0073948 A1    Mar. 17, 2016

Related U.S. Application Data

(63) Continuation-in-part of application No. PCT/US2014/027130, filed on Mar. 14, 2014.

(60) Provisional application No. 61/794,089, filed on Mar. 15, 2013.

(51) Int. Cl.
*A61B 5/055* (2006.01)
*A61B 5/00* (2006.01)
*G01R 33/56* (2006.01)

(52) U.S. Cl.
CPC .............. *A61B 5/055* (2013.01); *A61B 5/004* (2013.01); *A61B 5/4566* (2013.01); *A61B 2576/02* (2013.01); *G01R 33/5602* (2013.01)

(58) Field of Classification Search
None
See application file for complete search history.

(56) References Cited

U.S. PATENT DOCUMENTS

| 2008/0039710 A1* | 2/2008 | Majumdar ............ A61B 5/055 600/410 |
| 2016/0081578 A1 | 3/2016 | Gazit et al. |

OTHER PUBLICATIONS

The Role of Back Injury or Trauma in Lumbar Disc Degeneration an Exposure-Discordant Twin Study by Hancock et al. pub. Spine • vol. 35 • No. 21 • 2010 pp. 1925-1929 (Year: 2010).*
Determinants of Lumbar Disc Degeneration: A Study Relating Lifetime Exposures and Magnetic Resonance Imaging Findings in Identical Twins by Battie et al. pub.Spine• vol. 20 • No. 24 • 1995 pp. 2601-2612 (Year: 1995).*
Battie, M., et al., "The Twin Spine Study: Contributions to a changing view of disc degeneration", "The Spine Journal", 2009, pp. 47-59, vol. 9.

(Continued)

*Primary Examiner* — Katherine L Fernandez
*Assistant Examiner* — Michael S Kellogg
(74) *Attorney, Agent, or Firm* — Hultquist, PLLC; Steven J. Hultquist

(57) ABSTRACT

Systems, computer-readable media, and methods are described for assessing physiological condition of spinal intervertebral discs in a quantitative manner using magnetic resonance imaging (MRI) data A simple, objective, continuous measurement of disc health or degeneration/pathology is provided, using routinely acquired or other digital magnetic resonance imaging (MRI) sequences. The measurement includes calculation of a value based on one or more ratios from signal-based measurements of spinal disc structures or regions, which can be obtained either through manual tracing or automated through programming of image analysis software. The measurement can be implemented by a computer and/or stored on a computer readable storage medium.

3 Claims, 9 Drawing Sheets

(56) References Cited

OTHER PUBLICATIONS

Hancock, M., et al., "The Role of Back Injury or Trauma in Lumbar Disc Degeneration", "Spine", 2010, pp. 1925-1929, vol. 35, No. 21.
Note: For the non-patent literature citations that no month of publication is indicated, the year of publication is more than 1 year prior to the effective filing date of the present application.
Edited by Huber, G., et al., "Dependence of Spinal Segment Mechanics on Age and Posture", "Bundesanstalt fur Arbeitsschutz", Dec. 31, 2010, pp. 16-23.
Junno, J., et al., "Temporal Trends in Vertebral Size and Shape From Medieval to Modern-Day", "Plos One", Mar. 12, 2009, pp. 1-5, vol. 4, No. 3: e4836.
Beattie, P.F., et al., "Diffusion-Weighted Magnetic Resonance Imaging of Normal and Degenerative Lumbar Intervertebral Discs: A New Method to Potentially Quantify the Physiologic Effect of Physical Therapy Intervention", "Journal of Orthopaedic & Sports Physical Therapy", Feb. 2008, pp. 42-49, vol. 38, No. 2.

\* cited by examiner

NU210.4  MZ112.4  AN34.6
r1.87 + r4.57 = 6.44

NU121.3  MZ66.8  AN20.5
r1.81 + r3.26 = 5.07

NU50.4  MZ30.3  AN11.7
r1.66 + r2.59 = 4.25

NU111.8  MZ 61.0  AN25.4
r1.83 + r2.40 = 4.23

NU 85.7  MZ52.9  AN24.8
r1.62 + r2.13 = 3.75

NU19.1  MZ19.6  AN20.7
r -0.96 + r -0.96 = −1.92

FIG. 9A
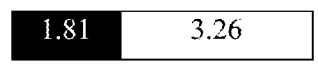
FIG. 9B
FIG. 9C
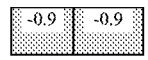
FIG. 9D
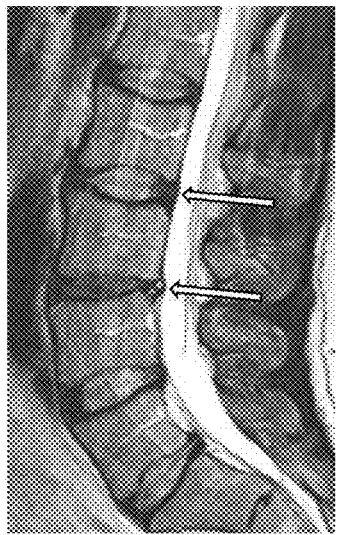 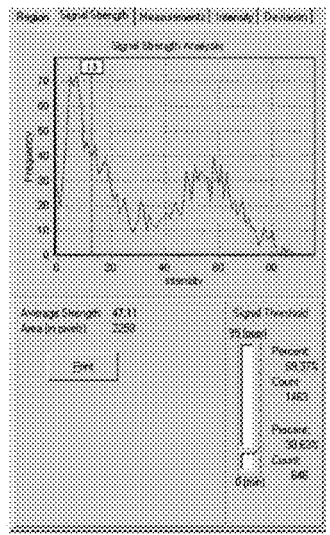 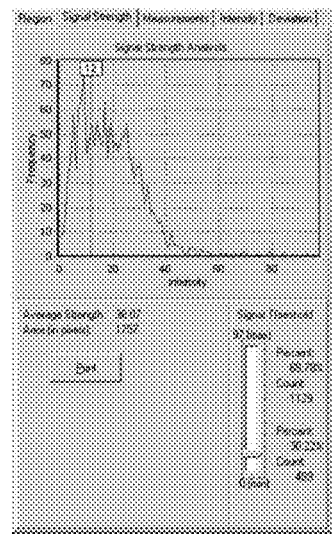
FIG. 10A      FIG. 10B      FIG. 10C

MEASURE OF DISC DEGENERATION AND PATHOLOGY

CROSS-REFERENCE TO RELATED APPLICATIONS

This application is a continuation-in-part under the provisions of 35 U.S.C. § 120 of International Patent Application No. PCT/US14/27130 filed Mar. 14, 2014, which in turn claims the benefit under 35 U.S.C. § 119 of U.S. Provisional Patent Application No. 61/794,089 filed Mar. 15, 2013 in the name of Keijo Tapio Videman for MEASURE OF DISC DEGENERATION AND PATHOLOGY. The disclosures of International Patent Application No. PCT/US14/27130 and U.S. Provisional Patent Application No. 61/794,089 are hereby incorporated herein by reference, in their respective entireties, for all purposes.

FIELD

The present disclosure relates to systems, computer-readable media, and methods for assessing physiological condition of spinal intervertebral discs in a quantitative manner using magnetic resonance imaging (MRI) data. The systems, media, and methods described herein provide a simple, objective, continuous measurement of disc 'health' or degeneration/pathology using routinely acquired digital MRI sequences. More specifically, they provide a calculation of a value based on one or more ratios from signal-based measurements of spinal disc structures or regions, which can be obtained either through manual tracing or automated through programming of image analysis software.

DESCRIPTION OF THE RELATED ART

The intervertebral disc is a major focal point of research and clinical investigation into back pain problems and other common spinal disorders, such as disc herniation and spinal stenosis, which are associated with disc degeneration. While the majority of patients seeking care for back pain complaints, estimated at around 85%, cannot be given a precise pathoanatomical diagnosis, the disc has long been suspected as a culprit. This suspicion drives vast amounts of clinical imaging and spine surgery. In fact, "degenerative disc disease" is currently the leading diagnosis associated with spine fusion in North America (Rajaee S S, Bae H W, Kanim L E, Delamarter R B Spine 37:67-76; 2012). Yet, the role of disc degeneration in common painful spinal disorders remains controversial. One factor limiting research and current knowledge of the relation of the disc to the onset and prognosis of painful spinal disorders is the quality and validity of measurements of disc degeneration and pathology.

Most current research on disc degeneration based on MR imaging uses visually evaluated 2 to 6 point ordinal scales of various degenerative signs. Kellgren J H and Lawrence J S (Ann Rheum Dis 16:494-502; 1957) introduced an x-ray based 5-point grading scale of osteoarthritis, including osteophytes and joint narrowing among other findings. However, the lumbar spine was "omitted because of difficulties with reproduction." Yet, osteophytes and disc narrowing became common elements of disc degeneration assessments used over subsequent decades, and disc bulging and signal loss were added later following the advent of MRI using T2 weighted images. These findings have been commonly included in numerous qualitative or visual assessments of disc degeneration, and have been considered individually or collectively through global disc degeneration scores. Schneiderman G, et al. (Spine 12:276-81; 1987) introduced a 4-point visual grading scale based on disc signal on MRI, which was then "validated" by comparison with discography scores on 36 patients. Approximately 15 years later, Pfirrmann C W and Resnick D (Radiology 219:368-374; 2001) created a gross 5-point ordinal scale for disc degeneration based on signal loss and heterogeneity and disc narrowing, which is currently widely used. The Pfirrmann scoring system has surprisingly high associations with age (an indicator of measurement validity), particularly in the upper lumbar discs, despite the grossness of the scale (shown in the validation section of this document). More recently, a "modified Pfirrmann" 8-point grading system was introduced, again based on disc signal and consideration of additional degrees of disc narrowing (Griffith J F, et al., Brit J Industr Med 32:E708-E712; 2007).

The most notable limitations of such qualitative rating systems of disc degeneration are lack of measurement precision and suboptimal measurement reliability. Other limitations include the frequent aggregation of different degenerative signs that may represent very different pathological or adaptive processes into global summary scores. For example, atrophic and proliferative changes as seen in disc narrowing and osteophytes of adjacent bone may have different determinants and differ in their clinical relevance, but have been combined into summary measures of disc degeneration (Sambrook P N, MacGregor A J, Spector T D. Arthritis Rheum 42:366-72; 1999). Such summary measures may dilute true associations that would be identified with specific measures.

Another significant challenge with most signal-based measures of disc degeneration is magnetic field heterogeneity, which influences signal and creates artifacts, particularly at the periphery of the field. Although the human brain is able to adjust visual assessment scoring to some extent to account for such variations due to signal strength within a sagittal image of a lumbar spine, for example, comparisons between scans and scanners are compromised. This problem has led some to adjust the signal of a particular structure or region of interest by an intra-body reference, such as adjacent cerebrospinal fluid (CSF), when using quantitative measurements (Battié M C, et al. Spine 20:2601-2612; 1995; Carragee E J, et al. Spine 34:2338-2345; 2009; Michopoulou S, et al. Acta Radiol 52:91-98; 2011). Visual assessments of one degenerative finding also can influence or bias the grading of other findings. For example, a narrowed disc may affect judgments of disc signal, bulging and osteophytosis, particularly when findings are marginal. In addition, all of the known qualitative grading systems use sagittal images, often the mid sagittal image, which samples a limited section of the disc.

Current quantitative disc degeneration measures using MRI data provide continuous or interval measurements, and are based largely on desiccation and loss of proteoglycans and collagens, but do not directly consider disc morphology and loss of structural integrity or annular disruption. When the signal on MRI T2-weighted sequence measures water concentration, the disc signal strength is theoretically an ideal measure of disc degeneration as indicated through desiccation. However, as mentioned above, unadjusted quantitative signal strength varies significantly between scans and scanners due to magnetic field inhomogeneity, individual anthropometrics and other factors. (Prott F J, et al. Radiother Oncol 37:221-224; 1995).

Antoniou J, et al. (Magn Reson Med 40:900-907; 1998) measured the content of proteoglycans, collagens and denatured collagens in the nucleus and annulus of 19 subjects (age range 19-79 years) and used T1 and T2 relaxation and magnetization transfer to "reflect . . . nucleus matrix composition of the disc" and its "structural integrity." In addition, "the apparent diffusion coefficient along the anterior-to-posterior axis of the nucleus" was correlated with the proteoglycan content using standard Siemens quantitative MR packages and showed some associations with age and Thompson's morphological grade (Antoniou J, et al. Spine 31:1547-1554; 2006). In another study, Nguyen A M, et al. (J Bone Joint Surg Am 90:796-802; 2008) concluded that T1rho relaxation time correlated with water content (r=0.53), glycosaminoglycan content and swelling pressure, and has potential as a quantitative biomarker of disc degeneration. Michopoulou (2011) applied texture analysis of medical images to quantification of lumbar disc degeneration from conventional T2 MR images. Such image-based quantification has similarities to an earlier method which counted signal differences between neighboring pixels and was associated with age similarly to obtain mean CSF-adjusted disc signal strengths. This earlier method considered the inhomogeneity and variation in magnetic field strength by adjusting the signal measures by the adjacent CSF signal, and while less than perfect, is clearly better than no adjustment (Videman, 2008).

NMR spectroscopy and high-resolution magnetic angle spinning (HR-MAS) techniques have been used to identify and measure disc biochemical substances, but do not directly measure disc matrix abnormalities and the measures also need to be adjusted for variation in magnetic field strength, as noted by a representative of NOCISCAN™. (Diagnostics, Data, Deformity. $7^{th}$ Annual Spine Technology Summit Oct. 23, 2013; Dallas). A 2011 article covered the main quantitative MR imaging measures in disc degeneration (Majumdar S, et al. J. Orthop Clin North Am 42:501-11; 2011).

Diffusion MRI and disc degeneration are less strongly associated than some of the earlier measures mentioned and diffusion MRI does not distinguish well between normal and degenerated discs (Niinimaki J, et al. Magn Reson Imaging 27:641-647; 2009). Furthermore, diffusion values are associated with biomechanical loading conditions. Diffusion imaging is also done with contrast agents, but these are unpractical and have not been shown to be clearly better than the other assessment methods mentioned (Majumdar, 2011).

In consequence, the art continues to seek improvements in technology for analysis of routine spinal images and improvement of the quality and validity of measurements of disc degeneration and pathology obtained from those images. Ideally, a disc degeneration measure would produce precise, accurate measurements with high reliability, reproducibility, and solid evidence supporting validity. In addition, the measurement would be available through standard clinical imaging and would reflect desiccation and loss of structural integrity of the disc. Furthermore, the measurements would be simple and quick to obtain, preferably through automated image analysis software.

SUMMARY

The present disclosure relates to systems, non-transitory computer-readable media, and methods for assessing physiological condition of spinal intervertebral discs in a quantitative manner using magnetic resonance imaging (MRI) data. Such systems, non-transitory computer-readable media, and methods enable a measure of spinal disc health to be generated, wherein the measure is calculated using one or more ratios from signal-based measurements of spinal disc structures or regions, which can be obtained either through manual tracing or automated through programming of image analysis software. The use of ratios of selected disc regions applies knowledge of disc pathogenesis: on T2 weighted MR images, when the inner region (nucleus) of the disc degenerates it loses signal, whereas the dark outer zone (outer annulus) of the disc eventually increases in signal with degeneration.

In one aspect, the disclosure relates to computer-implemented methods of automatically quantifying spinal disc degeneration, the computer-implemented method comprising: receiving at a computer system an imaging data set including digitized imaging data of at least one spinal area; the computer system automatically calculating a first mean signal intensity for a first region of the at least one spinal area included in the imaging data set; the computer system automatically calculating a second mean signal intensity for a second region of the at least one spinal area in the imaging data set; and the computer system calculating a first value comprising calculation of a ratio of the first mean signal intensity to the second mean signal intensity, and wherein the ratio is substantially independent of signal intensity heterogeneity of the imaging data set, wherein the first value is indicative of a degree of spinal disc degeneration for one or more spinal discs in the at least one spinal area.

In another aspect, the disclosure relates to measurement and inclusion of an intermediate region in the calculation.

In a further aspect, the disclosure relates to measurement and inclusion of signal intensity specifically from anterior and posterior regions of the spine. As an example, using an axial image of the disc, the computer system automatically divides the disc into two to four, or more, regions and calculates the regions' mean signal intensities (FIGS. 5A-B). In the simplest case of two regions, the mean signal strength of the first outermost peripheral region (anatomically "outer annulus") is the denominator and the mean signal strength of the second region (nucleus and inner annulus) is the numerator.

In a further aspect, the disclosure relates to measurement and inclusion of a specified portion of signal intensity pixels at the low end of the range within a region representing the entire disc on an axial or sagittal image, to represent the outer annulus. This technique can be applied by selecting the determined percent of pixels with the lowest intensity of the remaining pixels as the numerator. Such approach allows a simple ratio-based estimate of disc degeneration using based on internal disc structures.

A further aspect of the disclosure relates to a non-transitory computer-readable storage medium storing instructions executable by a computer system to automatically quantify spinal disc degeneration, the non-transitory computer-readable storage medium storing instructions to: receive at a computer system an imaging data set of digitized imaging data of at least one spinal area; calculate a first mean signal intensity for a first region of the at least one spinal area included in an imaging data set; calculate a second mean signal intensity for a second region of the at least one spinal area in the imaging data set; and calculate a first value comprising calculation of a ratio of the first mean signal intensity to the second mean signal intensity, wherein the first value is indicative of a degree of spinal disc degeneration for one or more spinal discs in the at least one spinal area, and wherein the ratio is substantially independent of signal intensity heterogeneity of the imaging data set.

A still further aspect of the disclosure relates to methods of assessing spinal disc health and obtaining a disc degeneration value, such methodology comprising the steps of: obtaining an MRI in digital form, determining the mean signal intensity of one or more nuclear regions, determining the mean signal intensity of one or more annular regions, and calculating a value representing disc health or a disc degeneration value, comprising calculation of one or more ratios of internal disc regions (e.g. a nuclear region to an annular region), using a computer-implemented analysis program comprising appertaining algorithm(s) for such calculation.

In another aspect, the disclosure relates to a therapeutic assessment and treatment method, comprising: obtaining selected MRI images of at least one spinal disc of a patient; digitizing the selected MRI images; selecting areas of the digitized images for input of corresponding area selections to a computer or other processor, for computational determination by the computer or other processor of a value indicative of spinal health of each of the at least one spinal disc of the patient based on at least one ratio of mean signal strength of a selected nuclear region to mean signal strength of a selected annular region of the at least one spinal disc of the patient; outputting by the computer or other processor of the value indicative of spinal health of each of the at least one spinal disc of the patient; and at least one of prescribing and conducting of therapeutic intervention comprising treatment of the patient, based on the outputted value indicative of spinal health of each of the at least one spinal disc of the patient.

In such method, the selecting of areas of the digitized image for input of corresponding area selections to a computer or other processor, may comprise manual tracing of areas of the digitized image. In other embodiments, the area selections are predetermined and computer-selected from the digitized images for input to the computer or other processor from an imaging apparatus. In still other embodiments, the therapeutic intervention comprises at least one of physical therapy and spinal disc surgery.

The disclosure in another aspect relates to an MRI imaging and computational system for determining spinal health of the patient, said system comprising: an MRI imaging apparatus configured to generate MRI images of at least one spinal disc of a patient and to digitize the MRI images; and a computer or other processor programmably configured to select areas of the digitized images for input of corresponding area selections to the computer or other processor, for computational determination by the computer or other processor of a value indicative of spinal health of each of the at least one spinal disc of the patient based on at least one ratio of mean signal strength of a selected nuclear region to mean signal strength of a selected annular region of the at least one spinal disc of the patient, and to output the value indicative of spinal health of each of the at least one spinal disc of the patient.

The MRI imaging and computational system may further comprise a database arranged to receive imaging data from the MRI imaging apparatus and computational data from the computer or other processor, for storage in the database, with the computer or other processor being configured to access the database and responsively generate from (i) newly generated patient data comprising at least one value indicative of spinal health of each of the at least one spinal disc of the patient, and (ii) archival data in the database, an output indicative of spinal disc health of the patient.

In such MRI imaging and computational system, the archival data in the database may comprise at least one of (a) historical spinal health disc data generated for the patient at a prior time or times, whereby the output comprises a longitudinal report of time-varying spinal disc health of the patient; (b) spinal health disc data for a patient population, whereby the output comprises a comparative report of spinal disc health of the patient in relation to the patient population, or a selected cohort sub-population thereof; (c) historical spinal health disc data generated for the patient at a prior time or times, wherein the computer or other processor is configured to generate a prognostic report for the patient comprising prognostic spinal disc health of the patient at a future time or times, based on the progression or character of prior spinal health disc data; and (d) spinal health disc data for a patient population, wherein the computer or other processor is configured to generate a prognostic report for the patient comprising prognostic spinal disc health of the patient at a future time or times, based on the progression or character of spinal health of the patient population, or a selected cohort subpopulation thereof. In other embodiments, the archival data in the database comprises at least two of archival data types (a)-(d).

The system as variously described above may comprise an MRI imaging apparatus configured to conduct T2 mapping of at least one spinal disc of the patient.

Other aspects, features, and advantages of the disclosure will be more fully apparent from the ensuing disclosure and claims.

BRIEF DESCRIPTION OF THE DRAWINGS

FIG. 4A provides an axial view image of a healthy disc with a brighter nucleus and darker annulus. FIG. 4B shows the fibrous rings of the annulus with concentric and radial tears in white, particularly in the posterolateral portion of the annulus. FIG. 4C provides a sagittal view of the lower lumbar spine with discography using barium sulphate, showing that the nucleus is well contained by an intact annulus in the highest disc (L3/L4) and substantial disc degeneration and associated annular disruption can be seen in the lower two discs.

FIG. 5A illustrates an oval light grey zone that represents the sum of nucleus and intermediate areas and a black area that represents the annulus. The arrows illustrate a SpIn1 ratio obtained by a method of the invention. FIG. 5B illustrates the outer annulus as black, the nucleus as white and the intermediate area as dark grey. The arrows illustrate a SpIn2 ratio obtained by a method of the invention. FIG. 5C illustrates an alternative SpIn2 ratio obtained by another method of the present disclosure.

FIGS. 9A-9D provide representations of four of the discs in FIG. 8, where 9A shows the disc of FIG. 8A, 9B shows the disc of FIG. 8B, 9C shows the disc of FIGS. 8E, and 9D shows the disc of FIG. 8F, where longer bars represent larger ratios and less degeneration. The signal ratio between the annulus and intermediate zone is represented in black and between the intermediate zone and nucleus in white.

FIG. 10A provides a magnetic resonance image of a spine, with upper and lower discs subject to measurement indicated by arrows; FIG. 10B provides a graph of the frequency of pixels by signal strength (intensity) of the upper disc in FIG. 10A; FIG. 10C provides a graph of the frequency of pixels by signal strength (intensity) of the lower disc in FIG. 10A.

FIG. 11A shows the results using on Pfirrmann scores and FIG. 11B shows the results using values calculated by methods of the invention.

DETAILED DESCRIPTION

Figure 1:
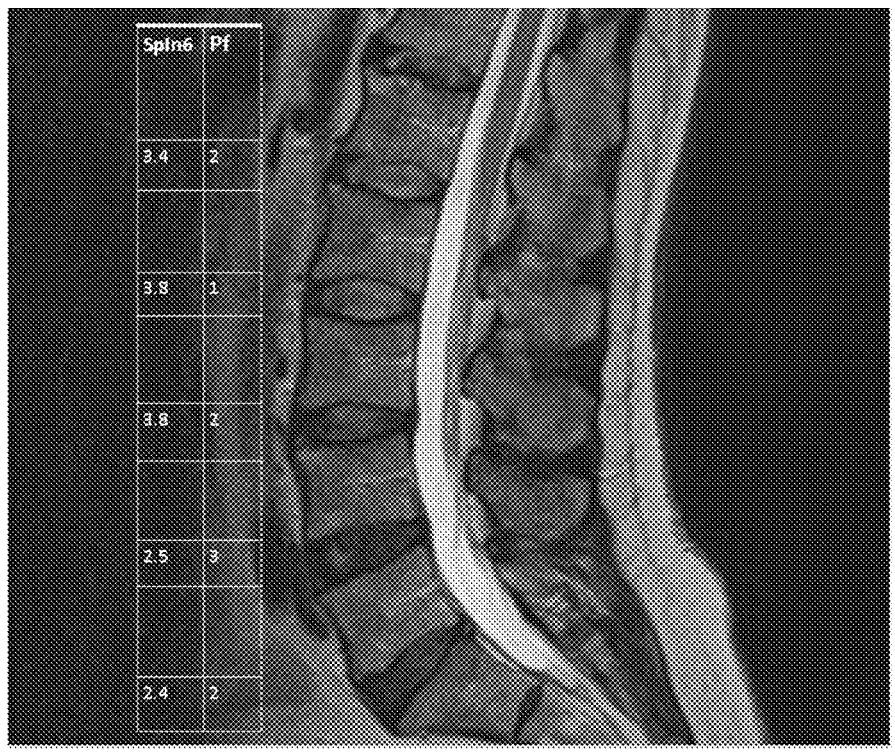
FIG. 1 provides a magnetic resonance image showing Pfirrmann (PF) scores in whole numbers (1-5) and scores obtained by the methods of the invention ("SpIn6"). A lower PF score and a higher invention value represent a healthier disc.

The present disclosure relates to systems, computer-readable media, and methods for assessing physiological condition of spinal intervertebral discs in a quantitative manner using magnetic resonance imaging (MRI) data. Such systems, media, and methods enable a measure of disc health to be generated, whose value is calculated from the signal intensities of various disc structures, as obtained from routine MRIs. The obtained value is useful as a measure in assessment of disc condition, diagnosis of disc health, and in determination of a therapeutic response, as well as in other applications such as research, risk-screening, prognosis, etc., as hereinafter more fully described.

As used herein, the term "substantially" in application to values and magnitudes refers to a variation in such values and magnitudes within a range of ±10%.

Ideally, a disc degeneration measure would produce precise, accurate measurements with high reliability and solid evidence supporting validity. In addition, the measurement would be available through standard clinical imaging and reflect desiccation and loss of structural integrity of the disc. Furthermore, the measurements would be simple and quick to obtain, preferably through automated image analysis software. The methods of the present disclosure, utilizing related measurements of disc degeneration and pathology, provide such a measure of disc degeneration.

Intervertebral discs are located between the vertebrae of the spine and, when healthy, function to provide flexibility to the spine and to resist spinal compression, through absorbing impacts to the spine that occur with simple activities conducted on a daily basis. Structurally, the disc is comprised of an outer area known as the annulus fibrosus (referred to herein as simply "annulus") which surrounds an inner area known as the nucleus pulposus (referred to herein as simply "nucleus").

The annulus of a disc is comprised of several layers of fibrocartilage that, when healthy, strongly contain the nucleus, which is an arrangement of loose fibers suspended in a mucoprotein gel. However, with disc degeneration, the fibrocartilage of the annulus can break down, developing tears and/or decreased thickness. Assessment and identification of such breakdown can be essential to diagnosis of disc degeneration.

As discussed in detail above, previously utilized methods of assessing disc degeneration possess numerous deficiencies. Known qualitative measures are not detailed enough in the grading systems utilized, and lack measurement precision and reliability and may be tinged with bias, based on correlated findings. Further, challenges of aggregation of different aspects of a condition exist. Still further, the equipment used for imaging presents additional limitations to scoring.

As an analogy of visual ordinal scales of disc degeneration, a similar ordinal or dichotomous scoring system could be applied to, e.g., measurement of aging by scoring hair color (black, dark gray, light gray or white), old appearance (yes or no) and wrinkles (none, little, moderate or much). It is seen that different degenerative signs do not necessarily go hand in hand. Summing of various qualitative ordinal scores to create a global rating is sometimes referred to as a 'semi-quantitative' measure, and while the range of possible scores is expanded, their nature as qualitative, gross visual assessments remains.

Additionally, known quantitative measures are also limited by variations in signal strength between scans and scanners due a number of factors.

Figure 3:
FIG. 3 provides comparative magnetic resonance images of a healthy spine on the left, showing a wide spinal canal providing good cerebra spinal fluid sample adjacent to the discs and a severely degenerated spine on the right.

One prior approach has been to use cerebrospinal fluid (CSF) for adjusting signal strength of manually segmented spine structures, such as discs, to create quantitative signal-based measures that can be compared between scans within and between individuals. (Videman, Gibbons, and Battié, 2008) However, with increasing degeneration of the lumbar spine and narrowing of the central canal with varying CSF flow, it can be difficult if not impossible to adequately visualize and obtain (segment) valid samples of CSF signal to use as an intra-body reference for disc signal adjustment (FIG. 3). In axial images good reference tissues have been missing because of the effects of CSF flow in the axial scan, making CSF signal an unreliable reference. In addition, the inhomogeneity and variation in magnetic field strength due to external factors, in particular in the periphery of the field, is an unresolved challenge in routine MR imaging and further in quantitative measures (Videman T, et al. Spine 33:2781-2788; 2008).

Figure 2:
FIG. 2 provides a magnetic resonance image of the lumbar region, showing Pfirrmann (PF) scores and scores obtained by the methods of the invention ("SpIn6"), where the PF grading results in the same score for all observations and the SpIn6 scores show relative degeneration among the imaged discs.

The basic weakness of most commonly used visual measures is the gross scoring of degenerative signs, typically using 2 to 5-point scales that lack measurement precision, and frequent aggregation of findings that may represent different processes (FIGS. 1, 2, 11).

FIG. 1 provides a MRI showing the results obtained using both Pfirrmann (PF) scores and scores obtained by methods of the present disclosure. For purposes of direct comparison of the obtained scores, such that the larger score is the desired observed score, in the figure, the PF scores are provided in a manner that is reversed as opposed to the traditional manner, i.e., 4=1, 3=2, 2=1 and 1=4. It is observed that the PF scores are shown to use the full 0-4 point grading scale with regard to the observed disc signal, while the SpIn6 scores range from 3.8-2.4.

FIG. 2 provides a MRI of the lumbar region, showing Pfirrmann (PF) scores and scores obtained by the methods of the present disclosure ("SpIn6"), where the PF grading results in the same score for all observed discs, a maximum score of 4 for all five discs. However, the methods of the present disclosure result in SpIn6 scores that show relative degeneration among the imaged discs, providing identification of the L4-L5 disc as less degenerated (with a score of 2.1) than the discs located above it (with scores of 2.4, 2.6, and 2.5) and identification of the lowest disc as having the highest relative degeneration (with a score of 2.8).

Further, while the Pfirrmann scale may function efficiently in comparing discs within a single image, limitations may arise when an initial grading is made too high and subsequent gradings are made relative to the initial grading. In such a case, a practitioner using the 5-point Pfirrmann scale may have to grade discs with different levels of degeneracy all with the same maximum score. Further, the Pfirrmann scale possesses additional limitations with regard to comparing scores assigned from different images, from different machines and/or scored by different observers.

Experienced MRI assessors seem to be able to adjust their ratings, in part, for magnetic field inhomogeneity within images and differences between scanners. Yet, this continues to pose a challenge and some quantitative measures make no attempt to adjust for such variations. Using CSF signal adjustment improves most quantitative measures, as judged through their association with age (an indicator of validity), however, the varying flow of CSF causes significant errors, in particular when acquired from a sagittal scan of a narrowed spinal canal, an axial scan, or from spinal levels at the periphery of the scan. These limitations are present in all the measures of disc degeneration mentioned. Even the theoretically strong measures based on specific proteins and biochemical markers are missing good references for use with routine MR scanners.

The present disclosure provides an objective method of assessment of disc degeneration and methods of affirmatively evaluating and diagnosing the same through calculation of a value including a ratio of relative signal intensities. The methods of the disclosure provide a solution to the substantial problem in known measurement systems, of adjusting for magnetic resonance field heterogeneity within an image and between images obtained from different magnetic resonance imagers.

In one aspect the disclosure provides a method utilizing assessment of signal strength of the nuclear region and the annular region of the disc. Pathogenesis of disc degeneration and pathology of the intervertebral disc and its depiction on magnetic resonance imaging (MRI) through typical changes in signal strength are known. In one aspect the methods of the disclosure utilize the relative intensities of mean signal strength (or standard deviation) of these regions on routinely acquired clinical MRI (or more sophisticated sequences) in digital form, to provide an assessment of disc degeneration or pathology.

The measure using the relative intensities also adjusts for magnetic field heterogeneity and inter-equipment variation, providing a measurement that can be compared between spinal levels and individuals. This principle can be applied to MR images acquired in the axial, sagittal, frontal or an oblique plane.

Figure 4A:
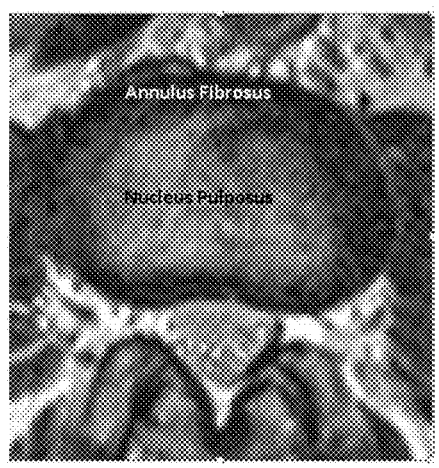
FIGS. 4A, 4B, and 4C provide comparative magnetic resonance images showing individual disc degeneration.
Figure 4B:
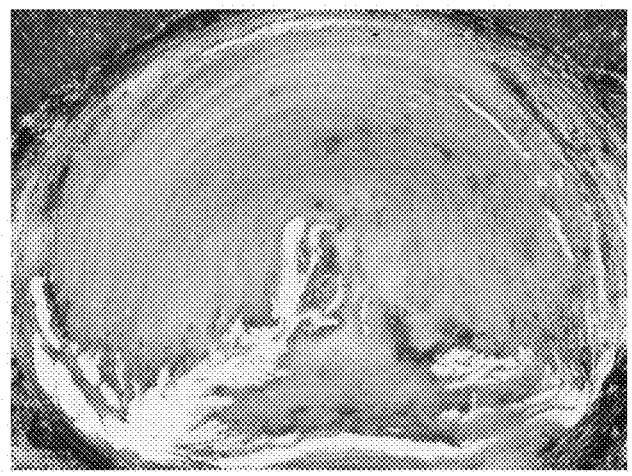
Figure 4C:

In the beginning of adulthood the annulus fibrosus zone of the intervertebral disc is dark and wide and the nucleus pulposus of the disc is bright in the T2 sequence on magnetic resonance images (the signal strength generally reflects hydration) (see FIGS. 4A, 4B, and 4C). During disc degeneration, the signal strength of the nucleus decreases and its area increases and the annulus zone becomes correspondingly narrower. The outer zone of the annulus continues to have very low signal strength, but with severe disc degeneration signal strength begins to increase. The phenomenon that the signal intensity of the nucleus decreases and that of the annulus increases slightly with progression of disc degeneration has been commonly observed and is well documented. (Antoniou, Pike, Steffen et al., 1998)

In a particular aspect the present disclosure provides a resultant value representing disc degeneration of a spinal disc imaged by MRI where the value is calculated from relative signal intensities of the nucleus and annulus of the disc. By calculation of the value, using a ratio of the intensities of areas of the disc, variations in signal intensity between images (attributable to imagers, operators, location in the body, specific patients, etc.) may be equalized. In another aspect the present disclosure provides measuring of the value. In a further aspect the present disclosure provides a method of diagnosing disc health using the resultant value.

Generally a method of the present disclosure includes the steps of: obtaining an MRI in digital form of any plane of the spine, though an axial or sagittal image is preferred, assessing the mean signal intensity of one or more nuclear regions, assessing the mean signal intensity of one or more annular regions, and calculating one or more ratios of a nuclear region to an annular region and providing the resultant value as an objective indicator of disc health, in which a computer-implemented analysis program comprising appertaining algorithm(s) for such calculation may be employed.

A magnetic resonance image (MRI) used in methods of the present disclosure is provided in digital form. Such MRI may be an axial image or may be a sagittal image.

Assessment of signal intensity in methods of the present disclosure is performed in order to obtain a mean signal intensity for an area of the disc. The area may be user defined, e.g. by manual tracing and the like, or may be automatically defined by a software program. Where software programs are utilized, it may be a program that is specially designed to automatically identify the segment regions of interest, and to obtain mean signal intensities within the identified areas. Alternatively a software program may be utilized that accepts the user defined area and determines the mean signal intensity for that area.

Figure 5A:
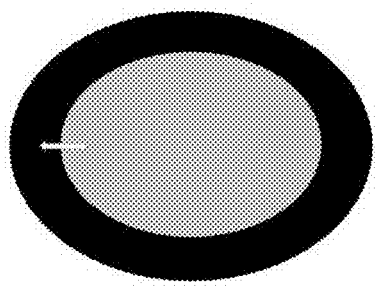
FIGS. 5A, 5B, and 5C provide a schematic of a disc in the axial plane.

One aspect of the present disclosure provides a method including calculation of a value including a ratio of the mean signal strength of a nuclear region divided by the mean signal strength of an annular region, as evaluated from an axial MRI image. In one aspect the nuclear region is comprised of just the nucleus itself and the annular region is comprised of just the annulus (FIG. 5A). In a further aspect, the nuclear region is comprised of the nucleus and at least a portion of one or more intermediate zones between the outer annulus and nucleus and the annular region is comprised of the annulus and at least a portion of one or more intermediate zones between the outer annulus and nucleus, where inclusion of the intermediate zone provides additional information on disc degeneration (FIG. 5B).

Figure 5B:
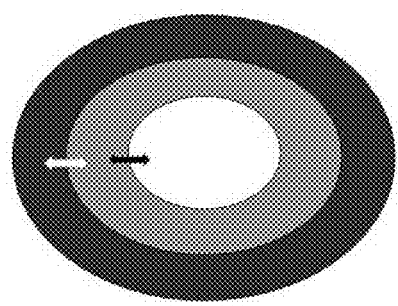
Figure 5C:
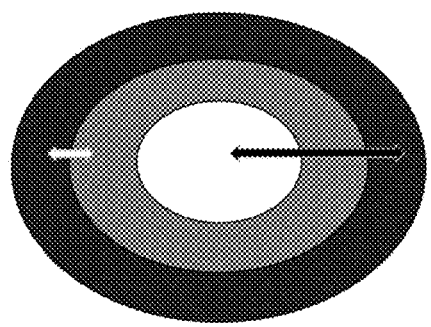

FIGS. 5A, 5B, and 5C provide a schematic of a disc in the axial plane. FIG. 5A illustrates an oval grey zone that represents the sum of nucleus and intermediate areas and a black area that represents the annulus. The arrow illustrates the ratio of the mean signal intensities of the two areas, which provides a simple disc degeneration measurement, termed SpIn1. In FIG. 5B the outer annulus is black, the nucleus is white and the intermediate area is grey. The size of the nuclear, intermediate and annular zones was determined by comparison to observations of the axial MRI of intervertebral discs of young adults with no signs of apparent disc degeneration. The arrows illustrate the ratios, which when summed provide a disc degeneration measurement, termed SpIn2. A disc degeneration measurement can also be obtained from the sum of the ratios of the outer annulus region with each of the nucleus and intermediate regions (FIG. 5C).

In a further aspect the present disclosure provides a method including calculation of a value including a ratio of the mean signal strength, as evaluated from a sagittal MRI image. In use of a sagittal image there are twice as many ratios calculated as from axial images, since anterior and posterior positions are separately evaluated and summed. As such, in one aspect the invention provides a method including calculation of a value that is a sum of a ratio of the mean signal strength of the nuclear region divided by the mean signal strength of the anterior annular region and the mean signal strength of the nuclear region divided by the mean signal strength of the posterior annular region. Alternatively, the mean signal strength of the sum of the anterior and posterior annular regions on sagittal images can be calculated to create a measure with the same number of ratios calculated as for the axial images.

Figure 6:
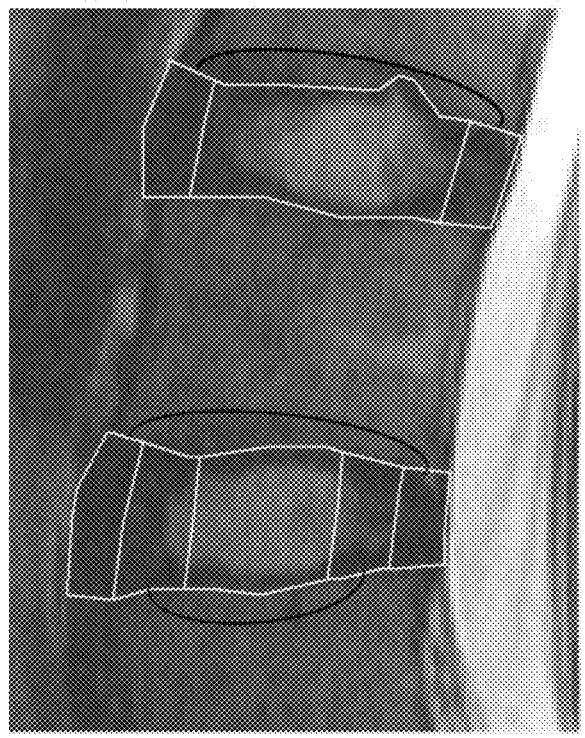
FIG. 6 provides an image showing an upper disc with a SpIn2 value calculated from the three identified zones (anterior annulus; nucleus and intermediate, posterior annulus) and a lower disc with a SpIn4 value calculated from the five identified zones (anterior annulus; anterior intermediate; central nucleus; posterior annulus; and posterior intermediate). Alternatively, the mean of the anterior and posterior annular regions (indicated by the black line) can be used to calculate a ratio value analogous a simple axial ratio value, and the mean of the anterior and posterior intermediate regions, as well as a mean of the anterior and posterior annulus regions (the lower disk), can be used to calculate a value using the same number of ratios comprising the analogous axial value representing disc health or disc degeneration.

In such method, the nuclear region is comprised of the nucleus and at least a portion of one or more intermediate regions between the outer annulus and nucleus and the anterior annular region is comprised of the anterior annulus and the posterior annular region is comprised of the posterior annulus. Alternatively, the mean signal strength of the sum of the anterior and posterior annular regions on sagittal images can be calculated to create a measure with the same number of ratios calculated as for the axial images. The method of the present disclosure provides a ratio or the sum of 2 ratios, also, termed SpIn2. FIG. 6 depicts a T2 image illustrating an aspect of the invention. In FIG. 6, the upper disc provides an illustration of a sagittal SpIn2 measurement, where the SpIn2 measurement is obtained by the sum of two obtained ratios in the anterior and posterior regions. Also in FIG. 6 the lower disc is divided into 5 areas: anterior and posterior annulus, anterior and posterior intermediate areas and the central nucleus area. The arrows illustrate 4 obtained ratios, which when summed provide the disc degeneration measure, SpIn4.

In various aspects the present disclosure provides a method including calculation of a value including a ratio from the determined signal intensities of the nuclear and annular regions, optionally containing intermediate regions and evaluating both anterior and posterior intensities, where the image is sagittal. In a still further aspect the present disclosure provides a method including calculation of a value that is a sum of ratios calculated from both axial and sagittal images. Table 1 provides exemplary ratios or measures obtained by the methods of the invention.

TABLE 1

| Measure abbreviation | Description of measures based on each areas mean signal strength |
| --- | --- |
| Axial SpIn1 | ([nucleus + intermediate]/[outer annulus]) |
| Axial SpIn2 | ([nucleus/intermediate] + [intermediate/outer annulus]) OR ([nucleus/outer annulus] + [intermediate/outer annulus]) |
| Sagittal SpIn2 | {nucleus + ([anterior + posterior intermediate]/2)/ ([posterior + anterior annulus]/2)} |
| Sagittal SpIn4 | [(nucleus/([anterior + posterior intermediate]/2) + ([anterior + posterior intermediate]/2)/ ([anterior + posterior annulus]/2) OR [(nucleus/+ ([anterior + posterior annulus]/2) + ([anterior + posterior intermediate]/2)/ ([anterior + posterior annulus]/2) |
| Sum SpIn6 | Standardized mean of ratios of the axial and sagittal ratios |

The calculated values of Table 1 are exemplary. All calculated values obtained by methods of the present disclosure include at least one ratio of the nuclear region to the annular region. The simplest measure involving the method is the ratio of the mean signal of the nuclear region (including the intermediate region) to that of the annular region (SpIn1). More complex measures combine more ratios of regions within the disc, such as the ratio of nuclear to intermediate regions and the ratio of intermediate to annular regions, and can also combine ratio measures of a disc from images acquired in multiple planes (e.g. axial and sagittal). In a further aspect a value of the present disclosure includes combination with other imaged disc characteristics such as, but not limited to, disc height and/or disc narrowing.

Thus, paired ratios from a sagittal image, such as the ratio of the posterior annular region and the anterior annular region (e.g. SpIn2) will result in a summed ratio measure approximately twice as large as a measure that is captured in one ratio from the axial image (e.g. SpIn1). This is not an issue when comparing like measures from like images. As such, similarly obtained ratios can be compared to one another, permitting comparative evaluation of disc degeneracy. Alternatively, the mean signal strength of the sum of the analogous anterior and posterior disc regions on sagittal images, such as the outer annular regions or intermediate regions, can be calculated to create a measure with the same number of ratios as for the axial images

[(nucleus+anterior intermediate/anterior annulus)]+
    [(nucleus+posterior intermediate/posterior annulus)]/2

OR nucleus/([anterior annulus+posterior annulus]/2)+
    ([anterior pulposus+posterior pulposus]/2)/([anterior annulus+posterior annulus]/2)

In another embodiment, measures from an axial image and a sagittal image from the same disc may be combined. Such combination requires standardization, e.g. SpIn6 in Table 1. In such aspect the resultant combined measurement provides slightly more information on the degenerative status of the disc because it provides information from more than one plane and incorporates information from each of those imaging planes that may or may not be available from an image taken of an alternate plane.

All measurements obtained by methods of the invention, whether obtained from a single obtained ratio or multiple such ratios, and/or from a single axial or sagittal image or multiple such images results in a final calculated value. The greater the relative degeneration of the discs, the smaller the resultant calculated value will be. As such, with progressive degeneration the mean signals of the nucleus and intermediate area/mean signal of the annulus area, as well as the slightly more complex signal-based disc degeneration measure's values (nucleus/intermediate area+intermediate area/annulus area) all decrease.

In implementation of the methods described herein, the methods may be implemented by a computer programmed to receive the required information and calculate a value as described herein. In one embodiment the process is automated by programming. In another embodiment the process requires input from a user to proceed to calculating the value.

In a further embodiment the invention relates to a non-transitory computer-readable storage medium storing instructions executable by a computer system to calculate a value as described herein.

Figure 7:
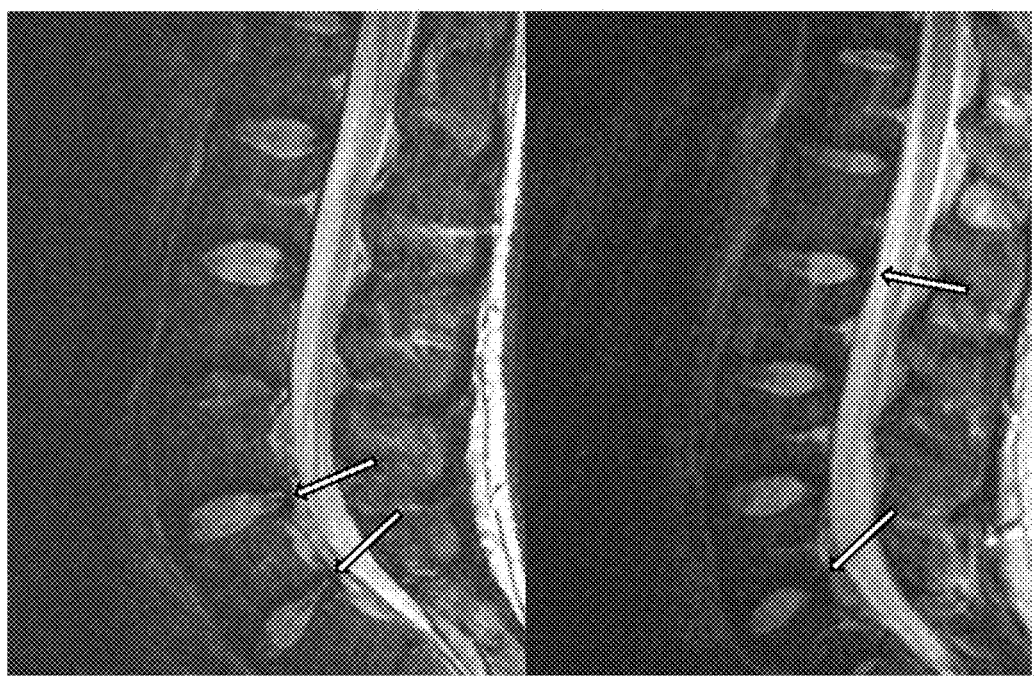
FIG. 7 provides comparative magnetic resonance images, wherein in the image on the left it is seen that the upper two discs have bright nuclei and thick annuli while the lowest two imaged discs have bright nuclei and thin annuli posteriorly (arrows). In the image on the right all imaged posterior annuli are thick (e.g., arrows).

In a young, healthy spinal disc, the whole nucleus is first very bright, surrounded by the gray narrow intermediate zone, followed by the dark annulus. When disc degeneration progresses, the gray intermediate zone widens and the bright nucleus area shrinks, respectively. In sagittal images one early sign of degeneration may be a dark cleft in the middle of the disc, running parallel to the upper and lower endplates. Also, when disc degeneration progresses, there may be a decrease in the thickness of the annular zone and the signal intensity of the annulus increases on T2-weighted MRI sequences, although it is poorly visualized in comparison to the more dramatic signal decrease typically seen in the nucleus. The increased signal in the annulus is likely the result of a loss of integrity of the annular structures, such as collagen fibers breaking, with resultant delamination with concentric and radiating tears (FIGS. 4A, 4B, and 4C), which may allow highly hydrated granulation tissue to grow into the annulus, as well as the spread of more hydrated nuclear material into the annulus, leading to an increase of signal strength (FIG. 7). In FIG. 7, in the left MR T2 image the upper two discs have bright nuclei and thick annuli; the dark disc and the two below with bright nuclei have thin annuli posteriorly (arrows). In the right MR T2 image all posterior annuli are thick (two of them indicated with arrows). In addition, calcification can be seen in severely degenerated discs, adding areas of high signal to the outer annulus.

The measurements obtained by methods of the present disclosure may therefore be influenced by the thickness of the annulus, whether viewed and measured on axial or sagittal images. In one aspect when repeated imaging and measurements are obtained over a period of time, the original or prior metrics of the annulus region (following development and prior to disc degeneration) are known for the subject, permitting direct comparison with later measurements of the disc to determine changes in disc degeneration or pathology from SpIn values unique to that individual.

In one embodiment, the measurements obtained are useful in obtaining a disc degeneration value and in another embodiment the measurements are useful in diagnosing spinal disc health.

Once measurements are obtained by methods of the present disclosure, such measurements may be used to assess disc health. In one aspect, measurements taken before disc degeneration and after disc degeneration would be obtained from the same individual and would be compared to identify the specific decrease in value attributable to such disc degeneration, providing clear evidence of onset or progression of disc degeneration. In such comparison, the original annular region (prior to degeneration) would be the ideal denominator for the measurement of subsequent disc degeneration.

In another aspect, where comparative measurements taken before disc degeneration in the same individual are not available, the obtained measurements after disc degeneration may be compared to measurements obtained from a large population sample of relatively young, "non-degenerated" discs which, taken together provide a reasonable average 'healthy' value for each of the regions of interest, such that similar measurements can be compared (e.g., SpIn1 from an axial image after degeneration compared to a SpIn1 average value from a large population of known healthy discs). Example 1 herein provides an example of obtaining a large reference population from healthy individuals.

Figure 8A:
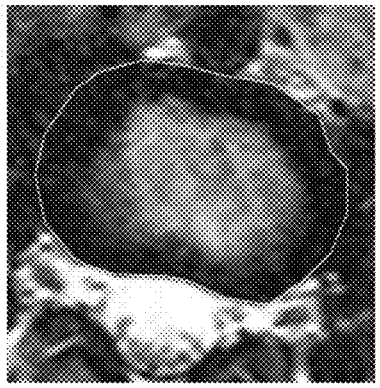
FIGS. 8A-8F provides axial disc images with degeneration values calculated by methods of the invention, where the values decrease with degeneration from a high value of 6.44 (FIG. 8A, upper left) to a low value of −1.92 (FIG. 8F, lower right).
Figure 8B:
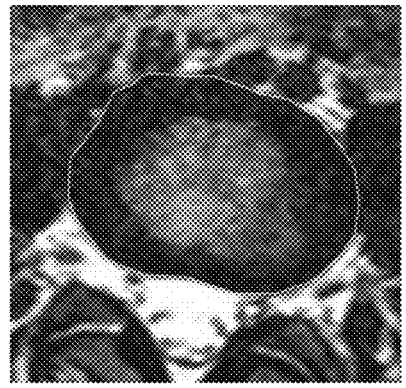
Figure 8C:
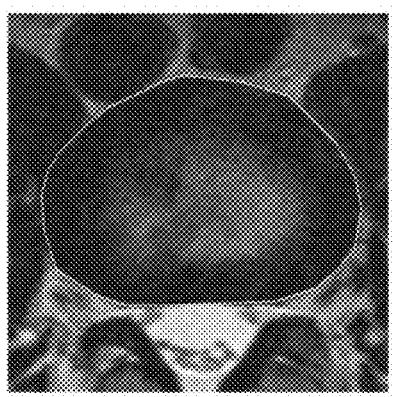
Figure 8D:
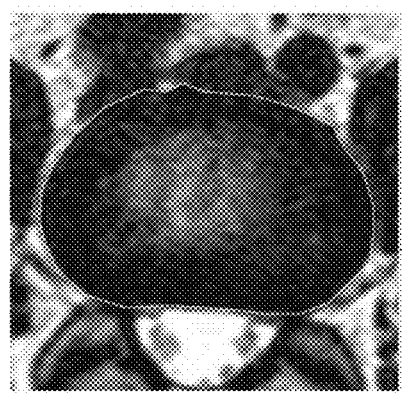
Figure 8E:
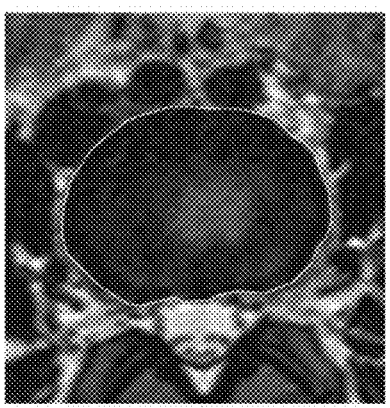
Figure 8F:
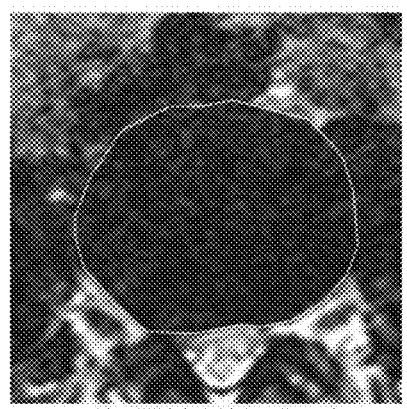

FIGS. 8A-F depict axial disc images showing signal variations associated with progressively greater disc degeneration. In each of the figures, "NU" represents the nuclear region signal strength, "MZ" represents the intermediate zone signal strength and "AN" represents the annular region signal strength. The first "r" value in each figure is the ratio between the signal intensities of NU and MZ, and the second "r" value is the ratio between MZ and AN. The sum of the r values in bold is the SpIn2 ratio-based disc degeneration measurement value for that image. FIG. 8A provides a calculated SpIn2 value of 6.44 where the healthy disc displays a high nuclear region intensity of 210.4, an intermediate signal of 112.4 and an annular region signal of 24.6. By comparison, FIG. 8F provides a calculated SpIn2 value of −1.92 where the degenerated disc displays a low nuclear region intensity of 19.1, an intermediate signal of 19.8 and an annular region signal of 20.7. Because the annulus has slightly higher signal strength than either of the nuclear region or the intermediate zone, the resultant value has a negative measurement value.

The values calculated from the images of FIG. 8A, FIG. 8B, FIGS. 8E and 8F are represented in FIGS. 9A-D, respectively, where the ratios are visualized through the length of the bars in FIG. 9. The bars provide a visual depiction of the overall disc degeneration, as well as the relative representation of different regions of the disc. The bars (and the calculated values) permit comparison between discs in the same spine or in different individuals. The total length of the bar represents the degeneration measurement using the invention measure, with longer bars signifying less degeneration. The ratio of the annulus to the intermediate zone is in black and the ratio of the intermediate zone to the nucleus is in white. The gray bar of FIG. 9D represents negative ratios, seen in highly degenerated discs of FIG. 8F where the nucleus is less bright than the intermediate zone and/or the annulus is less dark than the intermediate zone.

Due to the large field of view in lumbar spine imaging (generally from 260 to 384 mm), the signal strength can decrease significantly in the periphery of the field. Because of the heterogeneity in magnetic field strength and its effects on signal, an intra-body reference of known composition close to the structure of interest is typically needed to adjust tissue signals and aid interpretation of signal variations. The inequalities in field strength not only make comparisons of signal intensity between discs in the same spine challenging, but also comparisons of signal based measures between individuals difficult. Cerebrospinal fluid adjacent to the disc has been used previously as an intra-body reference (Battié, Videman, Gibbons et al., 1995; Carragee, Don, Hurwitz et al., 2009b; Videman, Saarela, Kaprio et al., 2009), but has not been ideal (Videman, Gibbons, and Battie, 2008).

The methods of the present disclosure address the issue of signal strength variation without need for an intra-body reference. When the annulus region surrounds the disc area the mean distances of the structures to the coil are virtually the same. As such, whether the intensities are high or low, as influenced by heterogeneity of the magnetic field or variations between MRI equipment, using the ratio adjusts for these MRI variations. This resolves the effects of varying signal strengths of the magnetic fields on different discs. This is an important innovation and aspect to the success of the ratio based disc degeneration measures.

In one aspect the methods of the present disclosure are performed utilizing an axial view sample. In this aspect the axial view samples provide the largest area of the disc and provide a large amount of information regarding the imaged disc. The axial view provides an image that is preferable for identification of the nuclear and/or annular regions, optionally further including an intermediate region, where identification is manual or automatic through software and where the identification may further include tracing of the perimeter of the identified region in order to obtain a mean signal value within the perimeter. Such obtained mean signal value will be utilized in methods of the present disclosure, to obtain the nucleus/annulus ratio and calculate the resultant value.

In another aspect the methods of the present disclosure are performed utilizing a sagittal view sample. In this aspect the identification of the nuclear and/or annular regions, and optionally further including an intermediate region, is also manual or automatic through software. The identification will necessarily include identification of anterior and/or posterior regions of the disc and may further include tracing of the perimeter of the identified region in order to obtain a mean signal value within the perimeter. Such obtained mean signal value will be utilized in methods of the invention, to obtain the nucleus/annulus ratio and calculate the resultant value.

A combined measure using a sagittal MR image that also incorporates mean disc height is also useful in rectification of the issue of signal strength variation, since highly degenerated discs typically also exhibit disc narrowing. The two disc qualities of signal intensity ratio and height could be combined simply through multiplying the two values. Again, as with the ratio measure alone, a smaller value of the combined measure signifies more degeneration. This combined measure, or extension of the use of the invention measures, could be particularly useful in longitudinal studies with repeated MRI assessments.

As such, in a further embodiment the present disclosure provides a method including calculation of a value including a ratio from the determined signal intensities of the nuclear and annular regions, optionally containing intermediate regions and evaluating both anterior and posterior intensities, where the image is sagittal and where the calculation further includes multiplication of the ratio by the measured disc height.

In a still further aspect, the method of the present disclosure may be utilized in general form to obtain a gross measure of disc degeneration in a known degenerated disc. In such aspect the ratio calculation includes segmenting the entire disc by tracing around its perimeter to identify a perimeter region, where the mean signal of a percentage of the highest signal intensity pixels (representing the nucleus and intermediate zones) is divided by a percentage of the lowest signal intensity pixels (representing the annulus). In a particular aspect the percentage of the highest signal intensity pixels of the disc, e.g., 60-70%, represent the nucleus region, and the remaining percentage of the lowest signal intensity pixels represent the annular region, where 100% of the disc pixels' signal intensities are utilized in the calculation. This gross estimate of disc degeneration will be more prone to error in highly degenerated discs, as the mean intensities representing nucleus and annulus areas contributing to the calculation are based on pixel intensity values rather than defined regions. This gross estimate may be obtained from either axial or sagittal images. The calculation may further incorporate mean disc height. Such inclusion may serve to rectify the error in the gross estimate, since highly degenerated discs typically also exhibit disc narrowing. Where the method includes disc height, the calculation further includes multiplication of the ratio by the measured disc height. Such aspect of the present disclosure is particularly useful in longitudinal studies with repeated MRI assessments where the inclusion of disc height can compensate for assumptions made in error in the gross measure.

FIGS. 10A, 10B, and 10C provide a magnetic resonance image of a spine, with upper and lower discs subject to measurement indicated by arrows. FIG. 10B provides a graph of the frequency of pixels by signal strength (intensity) of the upper disc in FIG. 10A. The peak of pixels with lowest intensity is mainly from the annulus and the remaining pixels of higher intensity are mainly from the nucleus and intermediate zones. For purposes of calculation of a gross estimate of disc degeneration the mean signal of the lowest intensity pixels, (e.g. 30.63%), can be identified as the "annular region" and the mean signal strength of the remaining pixels would be the "nuclear region." These determined signal intensity values would be used in methods of the invention in calculation of a value including a ratio of the mean signal strength of a nuclear region divided by the mean signal strength of an annular region. FIG. 10C similarly provides a graph of the frequency of pixels by signal strength (intensity) of the lower (dark) disc in FIG. 10A. The signal strength intensity attributable to each region is not as clear in FIG. 10C as in FIG. 10B, due to the degeneracy of the disc and the corresponding darkening of the nucleus and brightening of the annulus. This demonstrates the difficulties in using simply the gross estimate in highly degenerated discs.

As described herein, the methods of the present disclosure provide an objective measure of spinal disc desiccation and loss of structural integrity, calculated as the ratio of the mean signal of the nuclear region to that of the annular region. The methods of the present disclosure utilize signal intensity, obtained from routine clinical MRI, such as T2-weighted images through use of image analysis software to automate and standardize signal intensity measurements.

Use of a method of the present disclosure, including obtaining a value from analysis of intra-disc regions, including obtaining a ratio between relative regions resolves the substantial problem of adjusting for MR field heterogeneity within an image and field strength between images obtained from different MR imagers, which is a problem with previously utilized methods. The obtained value provides a more precise, accurate, objective measurement than is available through current qualitative measures and allows meaningful comparisons of changes in a disc over time and comparison of differences between individuals, which is a current shortcoming of other available qualitative and quantitative measures of disc degeneration.

Methods of the present disclosure and the values obtained through such methods are useful to compare and evaluate disc status over time in a single patient but are also useful in diagnosis of the status of a disc in a subject, as compared to values obtained from other subjects.

In various embodiments, the present disclosure contemplates a computer-implemented method of automatically quantifying spinal disc degeneration, comprising: receiving at a computer system an imaging data set including digitized imaging data of at least one spinal area; the computer system automatically calculating a first mean signal intensity for a first region of the at least one spinal area included in the imaging data set; the computer system automatically calculating a second mean signal intensity for a second region of the at least one spinal area in the imaging data set; and the computer system calculating a first value comprising calculation of a ratio of the first mean signal intensity to the second mean signal intensity, and wherein the ratio is substantially independent of signal intensity heterogeneity of the imaging data set, wherein the first value is indicative of a degree of spinal disc degeneration for one or more spinal discs in the at least one spinal area.

In such method, the imaging data set may comprise a sagittal digital MRI image, and the method may further comprise: the computer system automatically calculating the second mean signal intensity as an anterior second mean signal intensity and a posterior second mean signal intensity; the computer system automatically calculating an intermediate mean signal intensity for an intermediate region of the at least one spinal area between the first region of the at least one spinal area and the second region of the at least one spinal area included in an imaging data set, wherein the calculation comprises calculation of an anterior intermediate mean signal intensity and a posterior intermediate mean signal intensity; the computer system calculating a first intermediate ratio of the first mean signal intensity and the anterior intermediate mean signal intensity to the anterior second mean signal intensity, wherein the ratio is substantially independent of the signal intensity heterogeneity of the imaging data set; and the computer system calculating a second intermediate ratio of the first mean signal intensity and the posterior intermediate mean signal intensity to the posterior second mean signal intensity, wherein the ratio is substantially independent of the signal intensity heterogeneity of the imaging data set, and wherein the first intermediate ratio and the second intermediate ratio are indicative of the degree of spinal disc degeneration for one or more spinal discs in the at least one spinal area.

Such computer-implemented method may further comprise adding the first intermediate ratio and the second intermediate ratio to generate a composite ratio value indicative of the degree of spinal disc degeneration in the at least one spinal area, and dividing the composite ratio value by two.

In other embodiments, other numbers of spinal areas, mean signal intensities, composite ratio values, and numbers of ratios included in the composite ratio value.

Alternatively, the analogous anterior and posterior disc regions on sagittal images, such as the outer annular regions, anteriorly and posteriorly, or the intermediate regions, anteriorly and posteriorly, are summed and the mean signal intensity of the summed regions is calculated. These mean signal intensities for the summed intermediate and summed outer annular regions are used in calculating the ratios of the disc regions of interest, which are indicative of the degree of spinal disc degeneration. This approach using sagittal images to calculate the ratio measurements, which are indicative of the degree of spinal disc degeneration, creates a measure with the same number of ratios as in the axial images. Using this approach, a composite ratio value obtained from a sagittal image does not need to be divided by two for comparison to the analogous axial composite ratio value.

In another aspect, the present disclosure relates to a magnetic resonance image processing system, comprising an apparatus for magnetic resonance imaging of spinal intervertebral disc(s) of a vertebrate subject and outputting of corresponding imaging data, an image storage server configured to store and manage in an imaging database the imaging data that is outputted by the apparatus, and an image processing workstation configured to generate from imaging data outputted by the apparatus or imaging data accessed from the image storage server at least one measure of the physiological condition of the spinal intervertebral disc(s) of the vertebrate subject, wherein the at least one measure comprises an SpIn measure.

In Example 1 below the methods of the present disclosure are validated, as compared to a large population of individuals of known healthy discs.

As noted herein, the methods of the present disclosure provide an objective measure of disc dessication and structural integrity (degeneration/pathology). Such calculated value provides a new grading system for disc degeneration. Such grading system will be useful for inclusion in radiology reports accompanying routine clinical spine imaging, for use in longitudinal studies (e.g., for FDA approval) of the effects on the disc of new spine surgical implants or devices, drugs, and the like, for other research on the intervertebral disc, such as studies of risk factors (causes) and progression (pathogenesis) of disc degeneration and for screening for risk of disc-related back problems if disc degeneration proves predictive of future problems. Such uses of the obtained values as a grading system for disc degeneration are exemplary and other such uses are contemplated by the inventor.

Still further, values obtained using methods of the present disclosure may be used to determine therapy for a subject presenting with back pain or other back issues. Where the value is used to affirmatively identify disc degeneration and the degree of such degeneration, an appropriate therapy can be identified and employed. Currently, therapies for degenerative disc disease may range from relatively conservative care, such as stretches, exercises and physical therapy, to more extreme therapies, such as spinal fusion or other surgical interventions. Identification of the degree of degeneration may allow a practitioner to more accurately identify the appropriate course of therapy.

The advantages and features of the present disclosure are further illustrated with reference to the following example, which not to be construed as in any way limiting the scope of the present disclosure but rather as illustrative of various embodiments in specific applications thereof.

Example 1

Validation of the SpIn Measures of Disc Degeneration

Validation of the claimed methods of the present disclosure and the obtained values was performed as follows. A first sample of 232 men (age 35-70 years) from the population-based Finnish Twin Cohort were each imaged; 108 of these subjects were reimaged 15 years later. Such images were MRI images of the lumbar spine. The first confirmatory sample including 87 men, each reimaged 10 years later. All subjects were imaged with Siemens' scanners and for the 107 and 87 subjects that were reimaged, Pfirrmann scores were also available.

Two confirmatory groups of 347 and 564 subjects, respectively, seeking care for painful back-related problems, ranging in age from 18 to 86 years, were imaged with one of three scanners (Phillips "Achieva"; Hitachi "Aperto" or Siemens "Avanto"). The MRI image included the lumbar region, in particular the L3-L4 disc.

To examine the construct validity of the values obtained (SpIn) from signal strength ratio calculations and associated with various aspects of disc degeneration, it was necessary to identify factors that are clearly and substantially associated with greater disc degeneration. It is known that degrees of degeneration are clearly associated with age but not fully dependent on age. Another factor of disc degeneration, which most clearly meets the desired criterion are genetic influences. It was theorized that a valid degenerative measure would correlate with both age and genetic influences. Familial aggregation within twin pairs can be used as a good proxy for heredity, given that no known influential shared exposures have clear effects in adulthood.

Five different SpIn measures (see, e.g., Table 1) were obtained and compared with 'Pfirrmann scale grading system' measurements of lumbar spine degeneration and previously used quantitative CSF-adjusted disc signals (Griffith, Wang, Antonio et al., 2007; Videman, Gibbons, and Battie, 2008; Michopoulou, Costaridou, Vlychou et al., 2011; Carragee, Don, Hurwitz et al., 2009a; Battié, Videman, Gibbons et al., 1995).

Figure 11A:
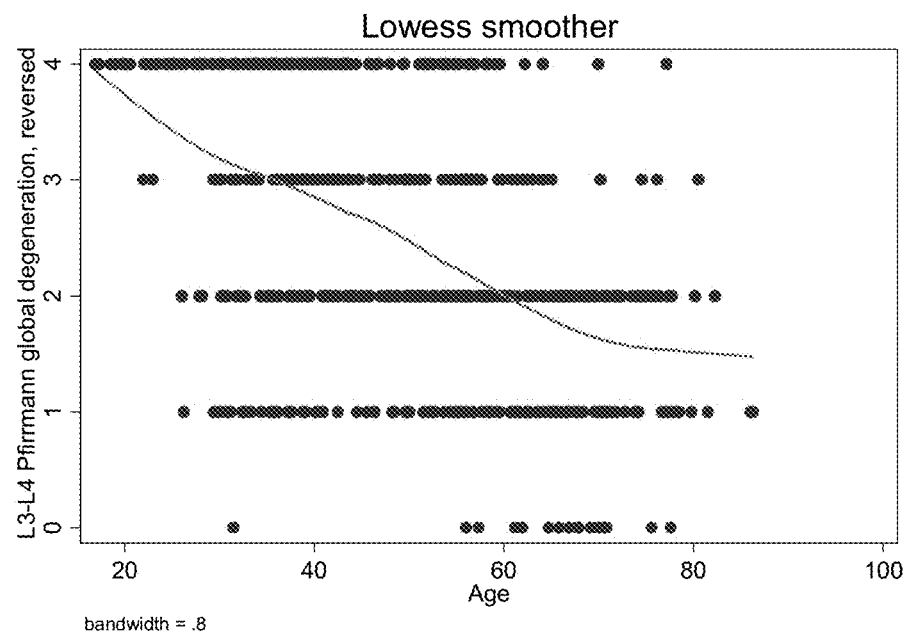
FIGS. 11A and 11B provide graphs showing the results of Example 1, where
Figure 11B:
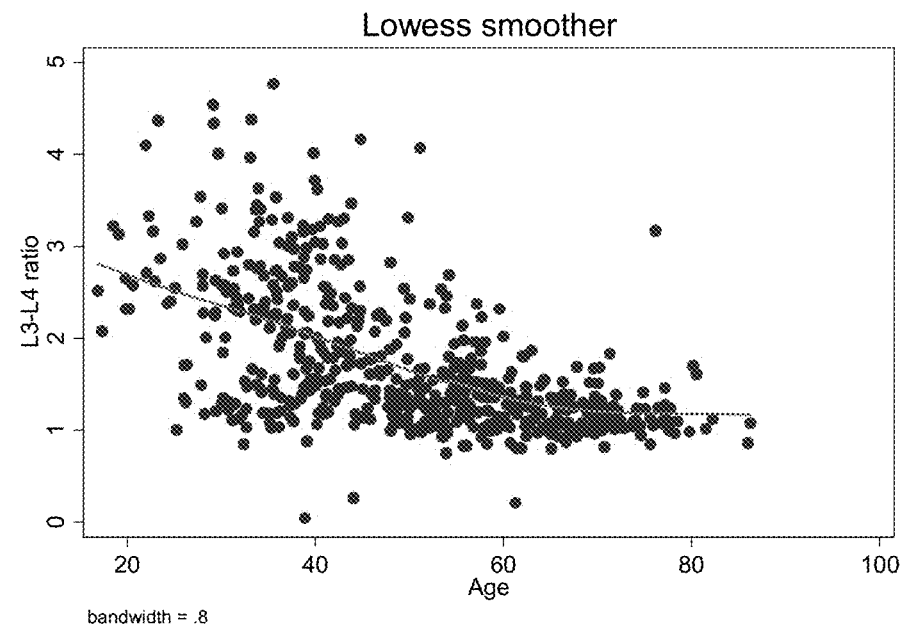
Figure 12:
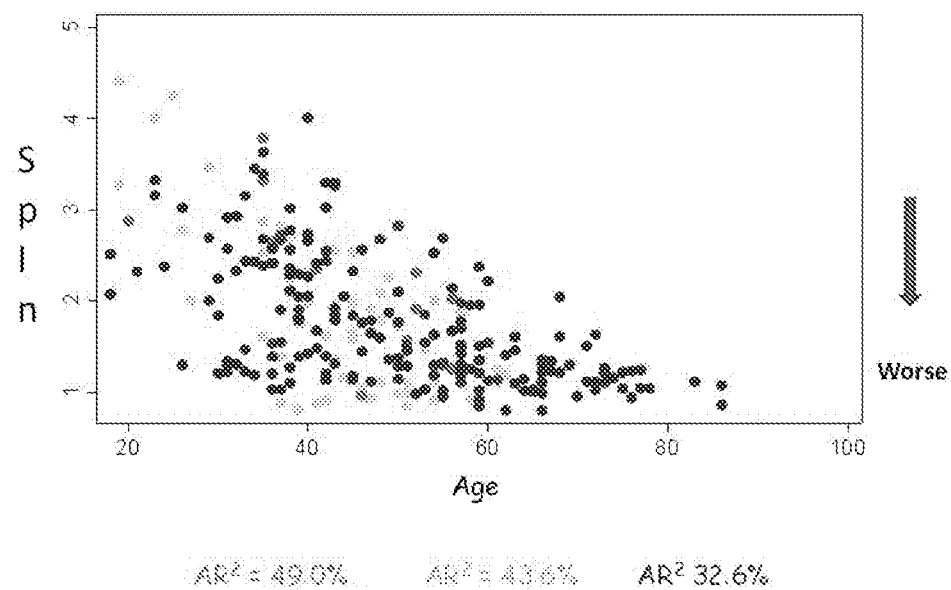
FIG. 12 provides a graph of the percent of variance ($AR^2$) in SpIn1 measures by Age from different scanners (in varying shades of gray). The graph supports the assertion that the scanner effect in the SpIn measures is very minimal.

FIG. 11A provides a graph of the Pfirrmann results in the 564 subjects, with respect to the L3-L4 disc. Such graph explains 26% of the variance in the Pfirrmann scores. The grouping of the results with an assigned 0 and 1 scores (on a reversed Pfirrmann 5-grade scale, with 0 being the most degenerate and 4 being healthy) in subjects older than about 65 shows a need for a score for a severely degenerated disc, presently beyond any score obtained with the Pfirrmann 5-grade scale. FIG. 11B provides a graph of the L3-L4 SpIn1 (nucleus/annulus ratio on an axial image) calculated value for this same population and explains 33% of the variance in the axial SpIn1. The figures are based on one disc (L3-L4) from 564 subjects. The age range was from 16 to 86 years. The L3-L4 disc in middle of the lumbar spine (and middle of MRI image). The biggest challenge is to measure most degenerated L4-5 and L5-S1 discs, where there are commonly more MRI artifacts, disc calcification and lumbar degenerative deformations.

The associations ($AR^2$) of SpIn measures with age and familiar aggregation are presented in Table 2 below. Generally it is seen that the $AR^2$ values are higher the larger the age-range is. The SpIn measures of axial and sagittal discs explained 29.5% to 13.7% ($AR^2$) of the variance by age in the sample of men within the range of 35 and 77 years (Table 2).

TABLE 2

Percent of Variance ($AR^2$) in Sagittal and Axial Quantitative ratio based measures by Age and Familiar Aggregation (n = 107)

| | Magnetom (baseline) | | Avanto (15-year) | |
|---|---|---|---|---|
| Scanner | Age only | Age adjusted Familiar aggregation | Age only | Age adjusted Familiar Aggregation |
| Axial SpIn1 | 23.4 | 43.6 | 21.5 | 46.7 |
| Axial SpIn2 | 26.6 | 38.7 | 22.9 | 43.8 |
| Sagittal SpIn1 | 13.7 | 49.2 | 18.7 | 49.0 |
| Sagittal SpIn4 | 21.8 | 53.5 | 22.4 | 43.4 |
| AxialSagittal SpIn6 | 29.5 | 42.1 | 23.4 | 42.8 |
| Sagittal CSF Adj Signal | 10.3 | 68.2 | 4.0 | 57.6 |
| Pfirrmann Score | 15.6 | 46.1 | 12.8 | 45.1 |

Age was most highly associated with the combined axial and sagittal summed SpIn6 measures, and most weakly associated with the sagittal SpIn2. The sum of the sagittal SpIn4 measures explained 53.5% of the variance in familial aggregation (and the axial SpIn2 measures explained the least (38.7%) (Table 2). Overall, SpIn measures from both axial and sagittal images that involved more disc regions and were most highly associated with age and familial aggregation, except that the sagittal CSF-adjusted disc signal had highest association with familial aggregation. However differences between the simplest (SpIn1) and most complex (SpIn6) measures were small. The sagittal CSF-adjusted disc signal had a lower association with age (Table 2).

The associations between age and the simplest axial SpIn measures (SpIn1) ($AR^2$=14.2%-15.6%) were clearly higher than age associations with Pfirrmann scores ($AR^2$=5.2%-13.2%) (Table 3). The age associations with both sagittal SpIn2 and SpIn4 were around 2 times higher than with Pfirrmann scores. The differences between SpIn measures and Pfirrmann scores were largest (2-3 times) in the two lowest disc levels where greater degeneration typically occurs (Tables 2 and 3). The associations of age with CSF-adjusted signal measures varied significantly by disc level and scanner, and were clearly lowest when using the Avanto scanner (Table 3). Images acquired with the Magnetom were of poor quality and lesser variance in both Pfirrmann scores and SpIn was explained by age than when using other MRI data sets (Table 3). The cross correlations between 3 measures show that, the CSF adjusted signal has the lowest correlation with all SpIn measures and the Pfirrmann scores correlations with SpIn measures ranged from r=0.47 to r=0.61 (Table 5).

TABLE 3

Percent of Variance (AR2) in Sagittal and Axial Quantitative ratio based measures by Age in Upper and lower discs separately (n = 107). The quality of Magnetom "5 yr" images was poor.

| | Scanner | | | | | |
|---|---|---|---|---|---|---|
| | Magnetom (baseline) | | Magnetom (5-year) | | Avanto (15-year) | |
| Disc levels | L1-L4 | L4-S1 | L1-L4 | L4-S1 | L1-L4 | L4-S1 |
| Axial SpIn1 | 15.6 | 16.3 | 4.0 | 11.9 | 14.2 | 14.9 |
| Axial SpIn2 | 18.7 | 17.2 | 5.2 | 13.7 | 15.8 | 14.4 |
| Sagittal SpIn2 | 12.7 | 5.2 | 15.0 | 10.4 | 12.4 | 11.1 |
| Sagittal SpIn4 | 20.9 | 11.2 | 13.5 | 17.4 | 15.4 | 15.6 |
| AxialSagittal | 24.6 | 17.1 | 10.1 | 17.8 | 15.3 | 17.2 |

TABLE 3-continued

Percent of Variance (AR2) in Sagittal and Axial Quantitative ratio based measures by Age in Upper and lower discs separately (n = 107). The quality of Magnetom "5 yr" images was poor.

| | Scanner | | | | | |
|---|---|---|---|---|---|---|
| | Magnetom (baseline) | | Magnetom (5-year) | | Avanto (15-year) | |
| Disc levels | L1-L4 | L4-S1 | L1-L4 | L4-S1 | L1-L4 | L4-S1 |
| SpIn6 Sagittal CSF Adj Signal | 9.9 | 6.3 | 13.9 | 6.5 | 3.1 | 2.8 |
| Pfirrmann Score | 11.4 | 8.8 | 6.7 | 6.6 | 13.2 | 5.2 |

TABLE 4

Based on Magnetom (N = 230 subjects) and on Magnetom Vision (N = 344)

| Measures | Age only | Scanner only | Age adjusted for scanner |
|---|---|---|---|
| Disc levels | | | |
| Axial SpIn1 | 19.2 | −0.2 | 19.3 |
| Axial SpIn2 | 20.4 | 0.1 | 20.7 |
| Sagittal SpIn2 | 11.7 | 11.4 | 13.0 |
| Sagittal SpIn4 | 18.1 | 13.6 | 19.8 |
| AxialSagittal SpIn6 | 23.8 | 3.5 | 24.8 |
| Sagittal CSF Adj Signal | 4.4 | 8.9 | 3.8 |
| Pfirrmann Score* | 12.6 | −0.3 | 12.5 |

*Cerebrospinal fluid

The variance explained by scanner type was 1-3% in axial SpIn measures and 11-14% on sagittal SpIn measures (the lowest percent is most useful measure) (Table 5).

TABLE 5

Correlations Between Ratios, Cerebrospinal Fluid Adjusted Signal and Pfirrmann Score

| Measures | Axial SpIn1 | Axial SpIn2 | Sagittal SpIn2 | Sagittal SpIn34 | Axial Sagittal SpIn6 | Sagittal CSF Adj Signal | Pfirrmann Score |
|---|---|---|---|---|---|---|---|
| Axial SpIn1 | 1.00 | | | | | | |
| Axial SpIn2 | 0.97 | 1.00 | | | | | |
| Sagittal SpIn2 | 0.56 | 0.55 | 1.00 | | | | |
| Sagittal SpIn4 | 0.66 | 0.67 | 0.94 | 1.00 | | | |
| AxialSagittal SpIn6 | 0.92 | 0.93 | 0.94 | 0.88 | 1.00 | | |
| Sagit CSF*) Adj Signal | 0.24 | 0.22 | −0.14 | −0.16 | 0.08 | 1.00 | |
| Pfirrmann Score | −0.61 | −0.57 | −0.47 | −0.53 | −0.61 | −0.36 | 1.00 |

The foregoing Example evidences the utility of the approach of the present disclosure in generating a viable measure of physiological condition of spinal intervertebral discs in a quantitative manner using magnetic resonance imaging (MRI) data.

Figure 13:
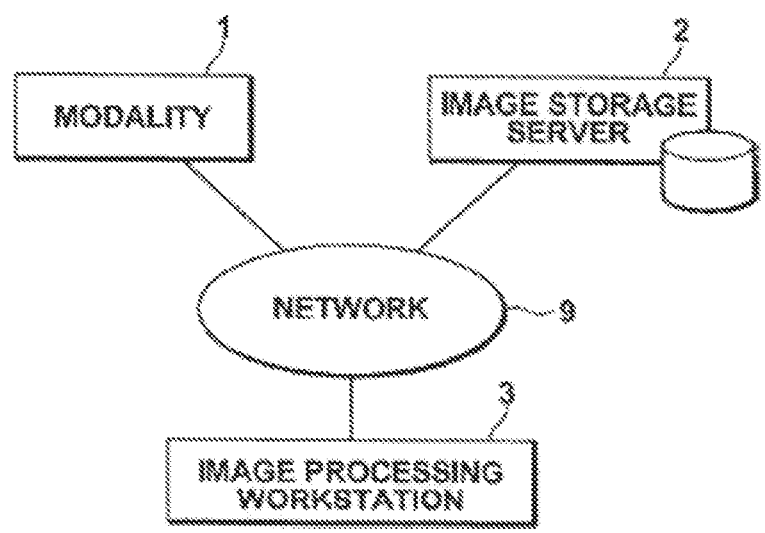
FIG. 13 is a schematic representation of a magnetic resonance image processing system according to one embodiment of the present disclosure.

FIG. 13 is a schematic representation of a magnetic resonance image processing system according to one embodiment of the present disclosure.

As depicted in FIG. 13, the system includes modality 1, image storage server 2, and image processing workstation 3 communicatively linked to each other via network 9.

The modality 1 is an apparatus for magnetic resonance imaging of spinal intervertebral disc(s) of a vertebrate subject, e.g., a human or veterinarian subject, to generate imaging data representing the region and outputting the image data. The modality 1 may include any suitable MRI equipment and assemblies. The imaging data may be outputted by addition of auxiliary information defined by DICOM (Digital Imaging and Communications in Medicine) standard as image information.

The image storage server 2 comprises a computer that is configured to store and manage in an imaging database the imaging data that is obtained by modality 1 as well as the imaging data comprising SpIn measures and correlative and ancillary data that are generated by the image processing workstation 3. The image storage server 2 may be configured in any suitable manner, and may comprise high capacity external storage media and devices and database management software, e.g., Object Relational Database (ORDB) management software.

The image processing workstation 3 is configured to generate the measures of the physiological condition of spinal intervertebral disc(s) as herein described, and may also be configured to generate correlative or ancillary output deriving from or otherwise related to such measures. For such purpose, the image processing workstation 3 is programmatically arranged with appropriate operating system and application software to process the imaging data that is obtained by modality 1, as accessed through the network 9, and to responsively generate such spinal condition measures and output. The spinal disc condition measures and output can be transmitted via the network 9 to the image storage server 2, and can be displayed on a display of the image processing workstation, or otherwise be exported from system in appropriate form.

The image processing workstation 3 may also be programmatically arranged to process imaging data that is stored in and accessed from image storage server 2, to provide appropriate output, e.g., longitudinal monitoring of deterioration or other temporal changes of condition of spinal intervertebral disc(s), or comparison of current condition data, as obtained from the modality 1, with a last-determined or time-averaged measure of disc condition, as obtained from image storage server 2.

The image processing workstation 3 may therefore be configured to enable a medical clinician to utilize the workstation for displaying disc condition measures, as well as correlative and ancillary output, for retrieving historical imaging data from the image storage server, and for information transmission of disc condition measures and associated output to recipient computers and clinicians via the network 9. For such purpose, the network 9 may be of any suitable character, and may comprise a local area network (LAN), global network such as a global Internet, and/or other network of a wired, wireless, or other character.

The image processing workstation 3 is appropriately configured for the functions described above, and may for example comprise a hardware configuration including a CPU, main memory, auxiliary memory, I/O interface, communication interface, input device (mouse, keyboard, and the like), display monitor, data bus, and the like, with a known operating system installed thereon. The imaging data processing conducted by the image processing workstation 3 may be carried out by execution of a spinal disc condition analysis program performing a methodology of the present disclosure to generate an imaging data processing output, e.g., an imaging data processing output comprising SpIn measures and optionally correlative and ancillary data, based on input imaging data from modality 1 and/or image storage server 2.

Such spinal disc condition analysis program may be installed or accessed from a suitable recording medium, such as a CD-ROM or the like, that is non-transitory and computer readable in character. The program may alternatively be downloaded and installed on the workstation from a storage device of a server linked to network 9, e.g., the image storage server 2, or other server accessible to the network 9, or by other independent network to which the workstation is communicationally linked. As a further alternative, the program may be partially or wholly embodied in firmware, or in other non-transitory computer-readable medium.

The imaging data storage format and communications between each component of the FIG. 13 system via the network 9 may be based on any suitable communications protocol, e.g., the DICOM protocol.

It will be recognized from the foregoing that the systems, computer-readable media, and methods described herein achieve a substantial advance in the art for assessing physiological condition of spinal intervertebral discs in a quantitative manner using magnetic resonance imaging (MRI) data, and that such systems, media, and methods may be implemented in a wide variety of applications. Such applications may include, for example, research applications, such as investigating determinants of disc degeneration and pathology and their progression, as well as screening for risk of back problems and spinal pathology, diagnosing spinal pathology, prognosing disc conditions and spinal health, monitoring and assessing effects of therapeutic interventions in spinal and disc treatments, etc.

In the use of the systems, computer-readable media, and methods described herein for assessing physiological condition of spinal inter-vertebral discs in a quantitative manner using MRI imaging data, imaging protocols may be of varied types, and may for example comprise (i) T2-weighted (or similar) sequences, (ii) T2 mapping determinations of distributions of T2 values at specific disc loci, or (iii) other protocols, such as combined T1 spin-lattice and T2 spin-spin relaxation quantitative techniques. Such techniques may be variously employed in the broad practice of the present disclosure, for determination of characteristics enabling assessment of disc hydration/desiccation, structural integrity, morphometric health, and longitudinal prognostic statistical probabilities involving spinal health.

The SpineInsight (SpIn) methodology described in the present disclosure embodies a substantial advance in the art, enabling an analytic solution to non-homogeneity errors in magnetic resonance imaging (MRI) signals, providing a continuous measure of disc degeneration from a fully healthy "perfect" disc to its ultimate calcification. The SpIn methodology of the present disclosure measures enables disc degeneration to be measured in disc annular and nuclear regions, and to establish reliable quantitative morphometrics of the disc that represent a great quantitative improvement over the gross measures and a suboptimal reliability of the Pfirrmann scale.

Although the Pfirrmann scale is a ubiquitous standard for grading of spinal discs, its lack of specificity and precision has entailed a high susceptibility to misdiagnosis and lack of effective intervention for adverse spinal health conditions of patients requiring therapeutic treatment. In this respect, degenerative disc disease is the leading diagnosis associated with spine fusion in the United States, underscoring the potential for patient harm when precise and accurate characterization of spinal discs is not achieved, as a result of the coarse grading of intervertebral discs on the basis of the Pfirrmann scale. Pfirrmann grading is based on disc signal strength and "visually" severe disc height decrease, and the annulus and nucleus to generations are not graded separately. By contrast, the SpIn methodology of the present disclosure enables quantitative characterization values based on all parts of the disc, as associated to both signal strength and to disc and vertebral morphometrics.

The associations between changes in SpIn values of the present disclosure and change in Pfirrmann grades with change in spine morphometrics after 15 years follow-up of initially evaluated patients, controlling for baseline age, height, and weight, are shown in the following table, wherein Pf=Pfirrmann scoring, and SpIn represents the quantitative determination methodology of the present disclosure.

| Change in L2-L4 spine morphometrics levels | SpIn p-value | Pf p-value |
| --- | --- | --- |
| Vertebra width | 0.002 | 0.28 |
| Vertebra height/width | 0.026 | 0.63 |
| Disc height | 0.001 | 0.26 |
| Disc area | 0.000 | 0.83 |
| Disc diameter | 0.000 | 0.92 |

It is apparent from the tabulated values that the Pfirrmann grading changes did not follow the morphometric changes to any degree as effectively as the SpIn methodology of the present disclosure.

Accordingly, the present disclosure in one aspect contemplates a methodology in which a clinician or other medical personnel obtains selected MRI images of at least one spinal disc of a patient, which images are then digitized, and in which the clinician or other medical personnel selects areas of the digitized images for input of corresponding area selections to a computer or other processor, for computational determination by the computer or other processor of a value indicative of spinal health of each of the at least one spinal disc of the patient based on at least one ratio of mean signal strength of a selected nuclear region to mean signal strength of a selected annular region of the at least one spinal disc of the patient, and outputting by the computer or other processor to the clinician or other medical personnel of the value indicative of spinal health of each of the at least one spinal disc of the patient, and at least one of prescription and conduct by the clinician of therapeutic intervention comprising treatment of the patient, based on the outputted value indicative of spinal health of each of the at least one spinal disc of the patient.

In other aspects, a variation of the foregoing methodology may be carried out, in which the clinician or other medical personnel traces, e.g., by manual tracing, areas of the digitized image for input of the corresponding area selections to the computer or other processor.

In still other aspects, a variation of the foregoing methodology may be carried out, in which the area selections for input to the computer or other processor are predetermined, and inputted by an imaging apparatus to the computer or other processor, e.g., at the time the selected MRI images are generated by the imaging apparatus.

In carrying out the foregoing methodology, the corresponding imaging and computational system may be interconnected in signal transmission relationship, so that imaging data are transmitted by the imaging apparatus to the computer or other processor contemporaneously with image generation by the imaging apparatus, or at a subsequent point in time. As previously described, the imaging and computational system may be constituted with a database, e.g., in a memory component of the computational apparatus, so that imaging and computational data are transmitted to the database for storage, and with the computer or other processor of the computational apparatus being configured to access the database and responsively generate, from newly generated patient data and archival data in the database, an output indicative of spinal disc health of the patient.

In various embodiments, the archival data in the database may comprise historical spinal health disc data generated by the methodology of the present disclosure for the same patient at a prior time or times, whereby the output comprises a longitudinal report of time-varying spinal disc health of the patient. In other embodiments, the archival data in the database may comprise spinal health disc data for a patient population generated by the methodology of the present disclosure, whereby the output comprises a comparative report of spinal disc health of the patient in relation to the patient population, or a selected cohort sub-population thereof. In still other embodiments, the archival data in the database may comprise historical spinal health disc data generated by the methodology of the present disclosure for the same patient at a prior time or times, wherein the computer or other processor of the computational apparatus is configured to generate a prognostic report for the patient comprising prognostic spinal disc health of the patient at a future time or times, based on the progression or character of prior spinal health disc data generated by the methodology of the present disclosure. Such prognostic report may alternatively be generated based on archival data in the database comprising spinal health disc data for a patient population generated by the methodology of the present disclosure, whereby the report is based on progression of spinal health for such patient population, or a selected cohort sub-population thereof.

The disclosure further contemplates imaging and computational systems configured to perform the various aspects and embodiments of the methodology described above, as well as non-transitory computer-readable storage media storing instructions executable by a computer system, which may comprise a computer or other processor, to quantify spinal disc health of a patient by any of the methodology aspects and embodiments described above.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A computer-implemented method of automatically quantifying and diagnosing spinal disc degeneration, the computer-implemented method comprising:
   receiving at a computer system an imaging data set including digitized imaging data of at least one spinal area;
   the computer system automatically calculating a first mean signal intensity for a first region of the at least one spinal area included in the imaging data set;
   the computer system automatically calculating a second mean signal intensity for a second region of the at least one spinal area in the imaging data set;
   the computer system calculating a first value comprising calculation of a ratio of the first mean signal intensity to the second mean signal intensity;
   the computer system automatically calculating a mean signal intensity for an intermediate region of the at least one spinal area between the first region of the at least one spinal area and the second region of the at least one spinal area included in the imaging data set;
   the computer system calculating a first intermediate ratio of the first mean signal intensity to the intermediate mean signal intensity; and
   the computer system calculating a second intermediate ratio of the intermediate mean signal intensity to the second mean signal intensity; and
   diagnosing a degree of disc degeneration based on the first intermediate ratio and the second intermediate ratio.

2. A computer-implemented method of automatically quantifying and diagnosing spinal disc degeneration, the computer-implemented method comprising:
   receiving at a computer system an imaging data set including digitized imaging data of at least one spinal area;
   the computer system automatically calculating a first mean signal intensity for a first region of the at least one spinal area included in the imaging data set;
   the computer system automatically calculating a second mean signal intensity for a second region of the at least one spinal area in the imaging data set;
   the computer system calculating a first value comprising calculation of a ratio of the first mean signal intensity to the second mean signal intensity;
   wherein the imaging data set is a sagittal digital magnetic resonance imaging (MRI) image or an axial digital MRI image,
   the computer system automatically calculating the second mean signal intensity as an anterior second mean signal intensity and a posterior second mean signal intensity;
   the computer system automatically calculating an intermediate mean signal intensity for an intermediate region of the at least one spinal area between the first region of the at least one spinal area and the second region of the at least one spinal area included in an imaging data set, wherein the calculation comprises calculation of an anterior intermediate mean signal intensity and a posterior intermediate mean signal intensity;

the computer system calculating a first intermediate ratio of the first mean signal intensity and the anterior intermediate mean signal intensity to the anterior second mean signal intensity the computer system calculating a second intermediate ratio of the first mean signal intensity and the posterior intermediate mean signal intensity to the posterior second mean signal intensity; and diagnosing a degree of disc degeneration based on the first intermediate ratio and the second intermediate ratio.

3. A computer-implemented method of automatically quantifying and diagnosing spinal disc degeneration, the computer-implemented method comprising:

receiving at a computer system an imaging data set including digitized imaging data of at least one spinal area;

the computer system automatically calculating a first mean signal intensity for a first region of the at least one spinal area included in the imaging data set;

the computer system automatically calculating a second mean signal intensity for a second region of the at least one spinal area in the imaging data set;

the computer system calculating a first value comprising calculation of a ratio of the first mean signal intensity to the second mean signal intensity;

wherein the imaging data set is a sagittal digital magnetic resonance imaging (MRI) image or an axial digital MRI image, the computer system automatically calculating the second mean signal intensity as an anterior second mean signal intensity and a posterior second mean signal intensity;

the computer system automatically calculating an intermediate mean signal intensity for an intermediate region of the at least one spinal area between the first region of the at least one spinal area and the second region of the at least one spinal area included in an imaging data set, wherein the calculation comprises calculation of an anterior intermediate mean signal intensity and a posterior intermediate mean signal intensity;

the computer system calculating a first intermediate ratio of the first mean signal intensity to the anterior intermediate mean signal intensity;

the computer system calculating a second intermediate ratio of the anterior intermediate mean signal intensity to the anterior second mean signal intensity;

the computer system calculating a third intermediate ratio of the first mean signal intensity to the posterior intermediate mean signal intensity;

the computer system calculating a fourth intermediate ratio of the posterior intermediate mean signal intensity to the posterior second mean signal intensity; and diagnosing a degree of disc degeneration based on the first intermediate ratio, the second intermediate ratio, the third intermediate ratio, and the fourth intermediate ratio.

* * * * *

UNITED STATES PATENT AND TRADEMARK OFFICE
CERTIFICATE OF CORRECTION

| | |
|---|---|
| PATENT NO. | : 11,272,856 B2 |
| APPLICATION NO. | : 14/855377 |
| DATED | : March 15, 2022 |
| INVENTOR(S) | : Videman |

It is certified that error appears in the above-identified patent and that said Letters Patent is hereby corrected as shown below:

In the Specification

Column 7, Line 28, "FIGS. 8E" should be -- FIG. 8E --.

Signed and Sealed this
Third Day of May, 2022

Katherine Kelly Vidal
*Director of the United States Patent and Trademark Office*